(12) United States Patent
Pudduck

(10) Patent No.: US 12,188,922 B2
(45) Date of Patent: Jan. 7, 2025

(54) CONTOURED SAMPLE PATH FOR FLUID ANALYZER

(71) Applicant: Siemens Healthcare Diagnostics Inc., Tarrytown, NY (US)

(72) Inventor: Christian Pudduck, Norfolk, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 1063 days.

(21) Appl. No.: 16/973,937

(22) PCT Filed: Jun. 20, 2019

(86) PCT No.: PCT/US2019/038153
§ 371 (c)(1),
(2) Date: Dec. 10, 2020

(87) PCT Pub. No.: WO2020/005692
PCT Pub. Date: Jan. 2, 2020

(65) Prior Publication Data
US 2021/0247380 A1 Aug. 12, 2021

Related U.S. Application Data

(60) Provisional application No. 62/692,061, filed on Jun. 29, 2018.

(51) Int. Cl.
*G01N 33/49* (2006.01)
*G01N 33/543* (2006.01)

(52) U.S. Cl.
CPC ....... *G01N 33/49* (2013.01); *G01N 33/54388* (2021.08)

(58) Field of Classification Search
CPC ............ G01N 33/49; G01N 33/54386; G01N 33/54388; G01N 33/4915; G01N 33/492
See application file for complete search history.

(56) References Cited

U.S. PATENT DOCUMENTS

| | | | |
|---|---|---|---|
| 3,884,640 | A | 5/1975 | Lock et al. |
| 4,871,439 | A | 10/1989 | Enzer et al. |

(Continued)

FOREIGN PATENT DOCUMENTS

| | | |
|---|---|---|
| JP | 2006003144 A | 1/2006 |
| WO | 2018114794 A1 | 6/2018 |

OTHER PUBLICATIONS

International Search Report and Written Opinion of International Application No. PCT/US2019/038153 dated Sep. 20, 2019.

(Continued)

*Primary Examiner* — Shogo Sasaki

(57) ABSTRACT

A sensor assembly for analysis of physical parameters and chemical constituents of small volume samples of bodily fluids. Disclosed herein is a sensor panel with an upper surface and a lower surface and at least one analyte sensor located on the lower surface. The sensor assembly also includes an optional adhesive layer and a contoured fluid pathway cutout. The upper surface of the adhesive layer is secured to the lower surface of the sensor panel. The sensor assembly also includes a sensor cartridge base with a fluid inlet and outlet and a contoured fluid pathway extending between the inlet and the outlet. The contoured fluid pathway mirrors the shape and span of the contoured fluid pathway cutout of the adhesive layer. As a fluid sample is input at the fluid inlet, the fluid traverses along the fluid pathway in contact with the at least one analyte sensor.

18 Claims, 3 Drawing Sheets

(56) References Cited

U.S. PATENT DOCUMENTS

| | | |
|---|---|---|
| 2006/0057030 A1 | 3/2006 | Lee et al. |
| 2006/0228258 A1 | 10/2006 | Samsoondar |
| 2007/0235335 A1 | 10/2007 | Strand et al. |
| 2008/0019866 A1 | 1/2008 | Paek et al. |
| 2009/0085071 A1 | 4/2009 | Brongersma et al. |
| 2016/0216284 A1 | 7/2016 | Misener et al. |
| 2017/0370904 A1 | 12/2017 | Zhang et al. |
| 2018/0111128 A1* | 4/2018 | Chatterjee .......... G01N 33/5302 |
| 2021/0318342 A1* | 10/2021 | Linbeck, III ..... G01N 35/00871 |

OTHER PUBLICATIONS

European Search Report and Written Opinion of European Application No. EP 19824469.1 dated Jun. 29, 2021.

\* cited by examiner

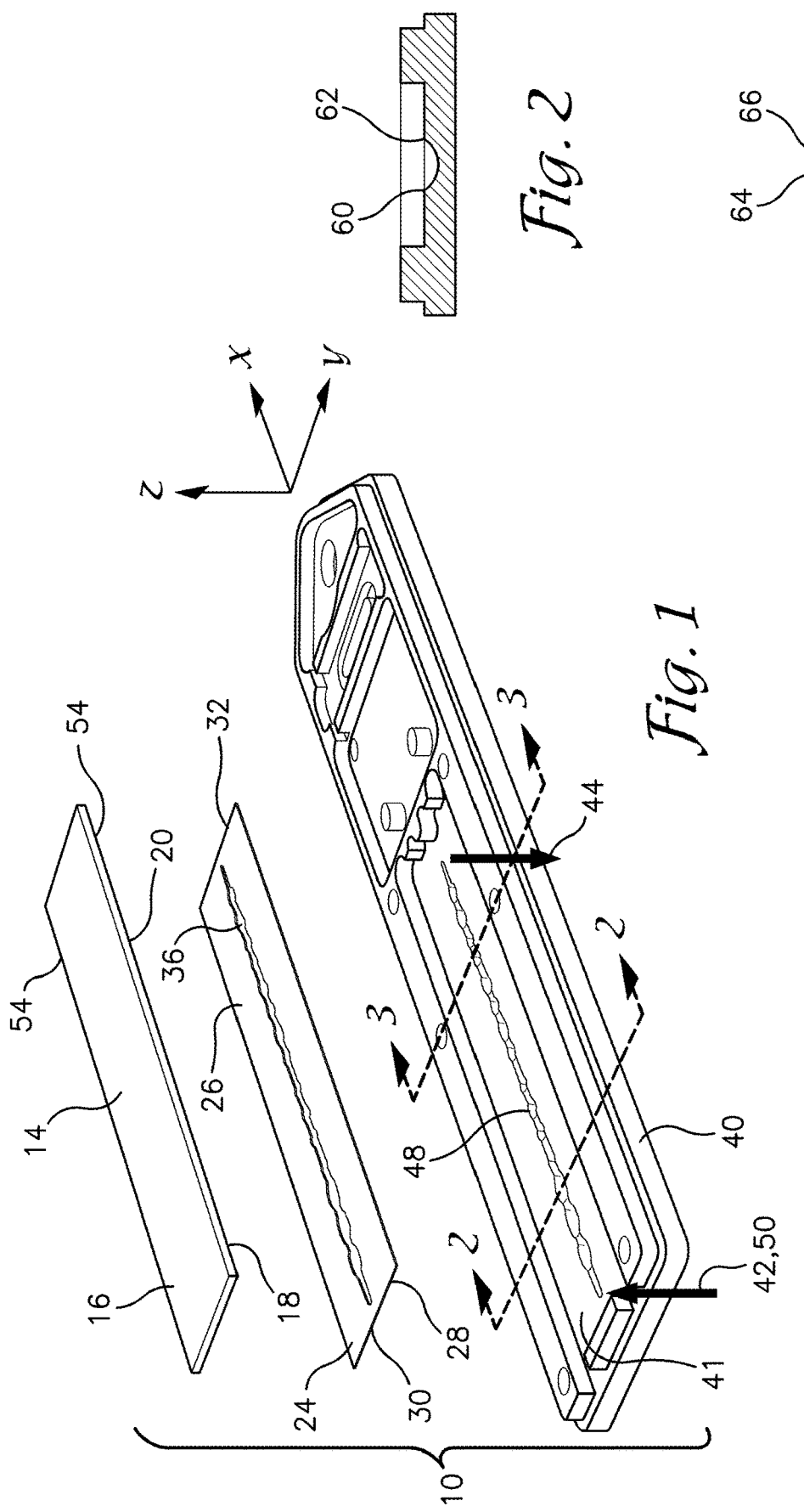

CONTOURED SAMPLE PATH FOR FLUID ANALYZER

The subject application claims benefit under 35 USC § 119(e) of U.S. provisional Application No. 62/692,061, filed Jun. 29, 2018. The entire contents of the above-referenced patent application are hereby expressly incorporated herein by reference.

FIELD OF THE DISCLOSURE

The disclosure herein relates generally to the field of sensors used in the analysis of fluid properties. The disclosed sensor assembly is embodied in a sensor cartridge which is especially adapted for use in biomedical applications so as to assist in the analysis of multiple physical parameters and/or chemical constituents of small volume samples of bodily fluids such as whole blood.

BACKGROUND

In a variety of instances it is desirable to measure the constituents in a bodily fluid to include, for example, partial pressure of blood gasses in a whole blood sample, concentrations of electrolytes in the blood sample, and the hematocrit value of the blood sample. For example, measuring $pCO_2$, $pO_2$, pH, $Na^+$, $K^+$, $Ca^{2+}$ and hematocrit value are primary clinical indications in assessing the condition of a medical patient. In addition, in an attempt to use as little of the patient's blood as possible in each analysis performed, the devices which are employed to analyze a blood sample are preferably relatively small. Performing blood analysis using a small blood sample is important, for example, when a relatively large number of samples must be taken in a relatively short amount of time or if the volume of blood is limited, as in neonates.

For example, patients in intensive care may require a sampling frequency of 15-20 per day for blood gas and clinical chemistry measurements, leading to a potentially large loss of blood during patient assessment. In addition, by reducing the size of the analyzer sufficiently to make the unit portable, analysis can be performed at the point of care. Also, reduced size typically means reduced turnaround time. Furthermore, in order to limit the number of tests which must be performed it is desirable to gather as much information as possible upon completion of each test. However, size limitations are imposed upon the sensors that are used to measure blood chemistry. These size limitations are in large part due to physical geometries of the sensors and the connections to the sensors.

Point of care blood gas analyzers permit in vitro analysis at the patient's bedside, in the emergency room, or in the intensive care unit. These units use solid state sensors with thin-film electrodes. The microchips, reagents, calibrators, and a sampling device are all contained within a disposable cartridge system. Healthcare facilities can select cartridges with additional test options, including potassium, glucose, BUN and lactate. Because whole blood can be tested, minimal specimen processing is needed: the sample does not have to be centrifuged and the plasma separated from the red blood cells prior to testing.

In settings with medium-to high volume sample testing, a multi-use cartridge system is used. These cartridges can be customized to the specific analyte menu and to the volume of testing. The number of samples measured on a cartridge may vary from 25 to 750 and once loaded into the analyzer, the cartridge typically has an in-use life of between 14 and 30 days.

The basic principle of operation for blood gas analyzers has not changed significantly from earlier units. In about 2005 self-contained cartridges were introduced into several analytical systems, paving the way for point of care testing and compact units. Whole blood can be analyzed for many analytes, including the electrolytes potassium ($K^+$), sodium ($Na^+$), and calcium ($Ca^{2+}$) and metabolites such as glucose, lactate, blood urea nitrogen (BUN), and creatine. The sensors used for these measurements are ion-specific or ion-selective electrodes (ISE). These sensors are membrane-based electrochemical transducers that respond to a specific ion. Biosensors are used in analyzers in the traditional clinical laboratory, but also in point-of-care testing devices. Biosensors convert the biochemical signal into an electrical signal.

Electrolytes are determined by potentiometric measurements, a form of electrochemical analysis. In potentiometry, the potential or voltage is measured between the two electrodes in a solution. These potentials can also be produced when a metal and ions of that metal are present in a solution. By using a membrane that is semipermeable to the ion, different concentrations of the ion can be separated. These systems use a reference and a measuring electrode. A constant voltage is applied to the reference electrode; the difference in voltage between the reference and measuring electrode is used to calculate the concentration of the ion in solution.

Ion-selective electrodes are based on a modification of the principle of potentiometry. The potential difference or electron flow is created by selectively transferring the ion to be measured from the sample solution to the membrane phase. The ion-selective electrode measures the free ion concentration of the desired analyte on a selectively produced membrane. Membranes have a complex composition and contain organic solvents, inert polymers, plasticizers, and ionophores wherein the ionophores are molecules that increase the membrane's permeability to the specific ion.

Amperometric methods measure the current flow produced from oxidation-reduction reactions. Types of amperometry include enzyme electrodes, such as the glucose oxidase method and the Clark $pO_2$ electrode. These types of designs are well known as biosensors and are adaptable for testing in the clinical laboratory as well as for point of care testing. Enzyme-based biosensor technology was first developed to measure blood glucose. A solution of glucose oxidase is placed between the gas permeable membrane of the $pO_2$ electrode and an outer membrane that is semipermeable. Glucose in the blood diffuses through the semipermeable membrane and reacts with the glucose oxidase. Glucose is converted by glucose oxidase to hydrogen peroxide and gluconic acid.

A polarizing voltage is applied to the electrode, which oxidizes the hydrogen peroxide and contributes to the loss of electrons. Oxygen is consumed near the surface of the $pO_2$ electrode and its rate of consumption is measured. The loss of electrons and rate of decrease of $pO_2$ is directly proportional to the glucose concentration in the sample. Enzyme-based biosensors are also used to measure cholesterol, creatine, and pyruvate.

The basic principles of operation for laboratory blood gas analyzers are the same as for the previously described electrodes for pH, $pCO_2$, and $pO_2$; and ion specific electrodes for the measurement of electrolytes. Approximately 50-120 µl of a well-mixed arterial blood sample are typically aspirated through the inlet and sample probe into the measuring chamber. The specimen then contacts the surface of each electrode for several seconds.

One of the principal challenges with existing sensor assemblies is that performing blood analysis using a small blood sample is important when a relatively large number of samples must be taken in a relatively short amount of time or if the volume of blood is limited, as in neonates.

Accordingly, it would be desirable to provide a sensor assembly which remains accurate over a relatively long period of exposure to electrolytes and blood samples, uses a very small sample size, detects the concentration of a number of different electrolytes as well as the partial pressure of a number of blood gases all in a single analysis.

SUMMARY

Heel sticks and draws from arterial lines are the most commonly used sites for blood draws. Heel sticks require a high degree of technical expertise to be done properly and without inflicting unnecessary pain or harm to the patient. Frequent blood draws for laboratory testing create the risk of iatrogenic anemia. It has been estimated that 64% of infants <1500 g receive transfusions for anemia due in part to frequent or excessive blood draws. With a plasma volume of 4-5% of body weight, a 1,500 g infant has a total of 70 mL of plasma. Blood transfusion may be required when 10% or more of a neonate's blood volume is withdrawn in 2-3 days. This amount represents about 80 mL/kg of body weight for a full-term infant, and about 100 mL/kg for a preterm infant.

The volume and number of blood draws have been reduced in recent years due to transcutaneous monitoring and newer equipment. Minimizing the volume of blood draws reduces the subsequent need for transfusion as well as the risk associated with transfusion. Many of the current clinical chemistry analyzers require small blood sample volumes for testing, with many sensor arrays requiring between 45 µL to 400 µL, depending on the number of analytes being measured (e.g., blood gases, electrolytes, etc.). The hematocrit of an infant can be >60%, reducing the volume of serum or plasma in the collection container. The "dead volume", consisting of the volume of specimen that must be in the instrument's sampling container, is required in addition to the specimen volume and must be minimal for neonatal applications.

It is an object of the sensor assembly disclosed herein to provide a low cost disposable sensor assembly.

It is a further object of the sensor assembly disclosed herein to compactly provide a disposable sensor assembly capable of housing a large number of analyte sensors.

It is a further object of the sensor assembly disclosed herein to provide a sensor assembly that requires a blood volume of about 30 µL.

These, together with other aspects of the disclosed sensor array, along with the various features of novelty that characterize the technology, are pointed out with particularity in the claims annexed hereto and form a part of this disclosed technology. For a better understanding of the disclosed technology, its operating advantages and the specific objects attained by its uses, reference should be made to the accompanying drawings and descriptive matter in which there are illustrated exemplary embodiments of the disclosed technology.

BRIEF DESCRIPTION OF THE DRAWINGS

Illustrative embodiments of the disclosed technology are described in detail below with reference to the attached drawing figures, which are incorporated by reference herein and wherein:

FIG. 1 is an exploded view of an embodiment of a sensor assembly;

FIG. 2 is a sectional view of the embodiment of the sensor assembly of FIG. 1 taken at line 2-2:

FIG. 3 is a sectional view of the embodiment of the sensor assembly of FIG. 1 taken at line 3-3:

DETAILED DESCRIPTION

Figure 4:
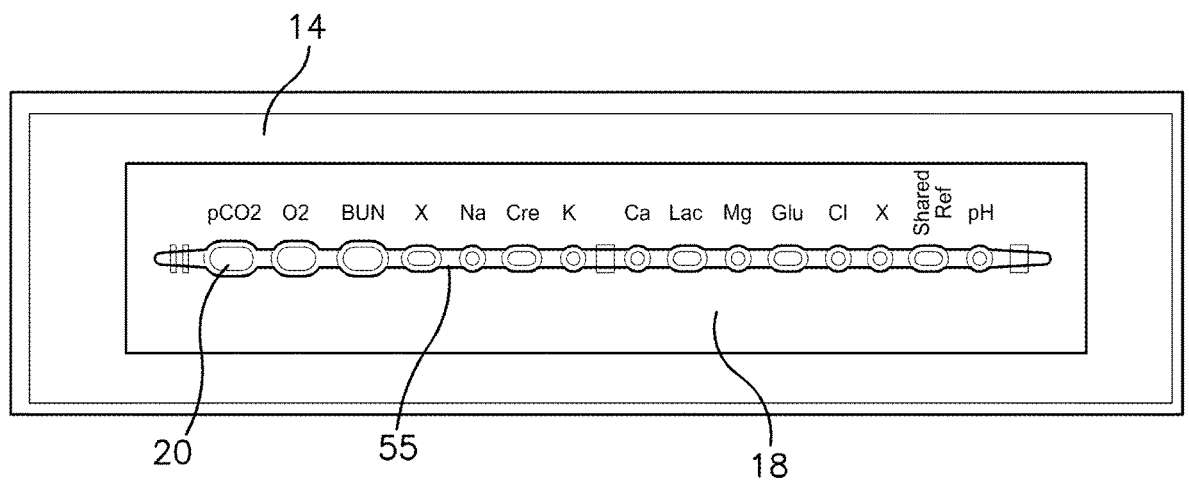
FIG. 4 is a plan view of the lower surface of the sensor panel detailing an assortment of analyte sensors.

Disclosed herein is an overhead sensor assembly 10 for determining partial pressures of gases, concentrations of electrolytes and metabolites in a fluid sample. Fluids, such as whole blood, can be analyzed for many analytes, including the electrolytes potassium ($K^+$), sodium ($Na^+$), and calcium ($Ca^{2+}$) and metabolites such as glucose, lactate, blood urea nitrogen (BUN), and creatine. The sensors used for these measurements are ion-specific or ion-selective electrodes.

The sensor assembly 10 is a component that is utilized within a cartridge that is wholly replaceable after a set number of fluid analyses have taken place or after the passage of a set amount of time. Disclosed herein is a subcomponent assembly that is central to the analysis of the fluid, and most importantly, is configured to minimize the volume of fluid, such as whole blood, that is required for analysis. Minimizing the volume of blood required for analysis is central to the inventive concept disclosed herein.

As seen in FIG. 1, a sensor assembly 10 for analysis of physical parameters and chemical constituents of small volume samples of bodily fluids is disclosed. The assembly 10 comprises a sensor panel 14 with an upper surface 16 and a lower surface 18 and at least one analyte sensor 20 located on the lower surface 18. The sensor panel 14 is preferably fabricated on a ceramic substrate: however, an engineered plastic substrate would function equally as well. In a preferred embodiment, the sensor assembly 10 utilizes an adhesive layer 24 with an upper surface 26 and a lower surface 28. The adhesive layer 24 utilizes first and second longitudinal edges 30, 32 and a contoured fluid pathway cutout 36 spanning proximate the first and second longitudinal edges 30, 32. The upper surface 16 of the adhesive layer 24 is adhesively secured to the lower surface 18 of the sensor panel 14. The lower surface 28 of the adhesive layer 24 is secured to an inset bed 41 of the sensor cartridge base 40. This disclosure contemplates that the adhesive layer 24 is optional and functionality of the sensor assembly 10 is not adversely impacted by elimination of the adhesive layer 24.

FIG. 1 reveals the sensor cartridge base 40 with a fluid inlet 42 and a fluid outlet 44 and a contoured fluid pathway 48 extending between the inlet 42 and the outlet 44. A set of coordinates revealing the X, Y and Z directions are also shown in FIG. 1 and serve to provide a basis for identifying orientation of a feature or claim element throughout this disclosure. The contoured fluid pathway 48 mirrors the shape and span of the contoured fluid pathway cutout 36 of the optional adhesive layer 24. A fluid sample 50 is input at the fluid inlet 42 and traverses along the fluid pathway 48 for contact with the at least one analyte sensor 20 before exiting at the fluid outlet 44.

The volumetric capacity of the contoured fluid pathway 48 between the fluid inlet 42 and the fluid outlet 44 is preferably in the range of from about 20 to 35 µl which is a de minimis amount. The need for a very small volume of fluid, as previously detailed, is central to this disclosure as blood draws from neonates, in particular, have been a significant driver for smaller blood volume analytical technologies.

The sensor assembly 10, in a preferred embodiment, utilizes a sensor panel 14 with at least two analyte sensors 20 located on the lower surface 18. Accompanying each analyte sensors 20 are at least two analyte sensor contacts 54. The sensor panel analyte contacts 54 are preferably located on the upper surface 16 of the sensor panel 14 and are laterally and oppositely disposed from one another across the contoured fluid pathway 48. Alternatively, the sensor contacts 54 may be located on the lower surface 18 of the sensor panel as is indicated in FIG. 1.

The sensor contacts 54 will be engaged by prepositioned leads (not shown) within the sensor cartridge assembly (not shown). A critical feature of the disclosed assembly is that dimensions of the contoured fluid pathway 48 increases, in one or both of the Y and Z directions, in close proximity to an analyte sensor 20 and reduces, in one or both of the Y and Z directions, when transitioning between analyte sensors. An exemplary transition area 55, between analyte sensors, can be seen in FIGS. 4, 5A and 5B. This narrowed transition area 55 between sensors 20 facilitates the reduced need for fluid volume in order to perform the desired analysis of the fluid. In an embodiment, the dimensions of the contoured fluid pathway 48 increases in the Y direction, in close proximity to an analyte sensor 20 and reduces in Y direction, when transitioning between analyte sensors while the dimension in the Z axis remains constant throughout the flow path. In a variation of this embodiment, the dimensions of the contoured flow path in the Z axis may also increase and decease along with the dimensions in the Y axis. In yet another illustrative embodiment, the dimensions of the contoured fluid pathway 48 increases in the Z direction, in close proximity to an analyte sensor 20 and reduces in Z direction, when transitioning between analyte sensors while the dimension in the Y axis remains constant throughout the flow path. In a variation of this embodiment, the dimensions of the contoured flow path in the Y axis may also increase and decease along with the dimensions in the Z axis.

FIG. 2 reveals an exemplary sectional view of FIG. 1 at sectional line 2-2. The sectional view at FIG. 2 reveals a rounded fluid flow path 48. Alternative configurations of the fluid flow path 48 are also contemplated by this disclosure. For example, a square, rectangular or, hexagonally shaped fluid flow path, among others, are also fully contemplated. The contoured fluid pathway 48 is comprised of a first upper edge 60 and a second upper edge 62. These edges 60, 62 are at the intersection of the walls of the fluid flow pathway 48 and the inset bed 41 of the cartridge base 40. The widest span between the first edge 60) and the second edge 62 is preferably in the range of about 0.300 to 0.600 mm; however, dimensions outside of this range are also contemplated by this disclosure.

FIG. 3 reveals a view of FIG. 1 at sectional line 3-3, at a point where the contoured fluid pathway narrows substantially such as the area seen at reference number 55 in FIG. 4. The contoured fluid pathway 48 in this instance is comprised of a first upper edge 64 and a second upper edge 66. These edges 64, 66 are at the intersection of the walls of the fluid flow pathway 48 and the inset bed 41 of the cartridge base 40. This narrowest span between the first upper edge 64 and the second upper edge 66 is in the range of 0.100 mm to 0.250 mm and the depth of the contoured fluid pathway 48 from the narrowest cross section to the widest cross section is in the range of from 0.200 to 0.400 mm.

The contoured fluid pathway 48 oscillates between a wider and narrower 55 span along the entire length of the pathway in order to minimize the amount of fluid required to pass beneath the analyte sensors 20 and yet maintain a sufficiently unrestricted fluidic connection in order to sustain fluid pressure to facilitate conveyance through the sensor assembly 10.

Though the term "beneath" may be used in describing the orientation of the fluid flow path 48 relative to the sensor location, this disclosure contemplates that the fluid flow path 48 may also be located above the analyte sensors 20 and the term "beneath" should not be considered limiting in that respect. The fluid path widens when in proximity to a sensor because a certain minimum surface area of the analyte sensor 20 must contact the fluid in order to take a reading. Where there are no sensors in the fluid path, there are no such surface area requirements and the fluid path narrows.

As seen in FIG. 4 the sensor assembly 10 is capable of analyzing a wide range of constituent concentrations and fluid parameters. The sensor assembly 10 disclosed herein includes analyte sensors 20 capable of measuring, for example, $pCO_2$, $O_2$, BUN, Na, Cre, K, Ca, Lac, Mg, Glu, Cl and pH. Though the sensors 20 are identified in a particular order in FIG. 4, this disclosure contemplates that the sensors may be ordered in many different configurations without impacting the functionality of the fluid analyzer.

Figure 5A:
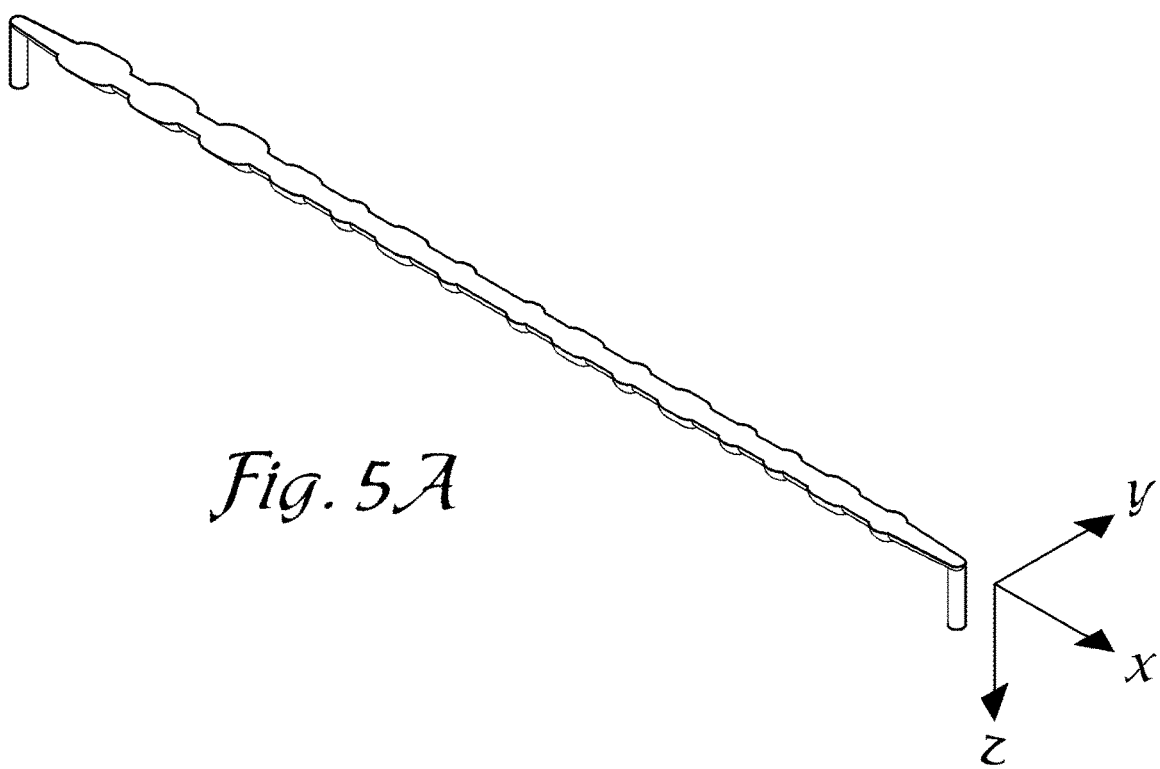
FIG. 5A is a perspective view of a fluid within the contoured fluid pathway of the sensor cartridge base.
Figure 5B:
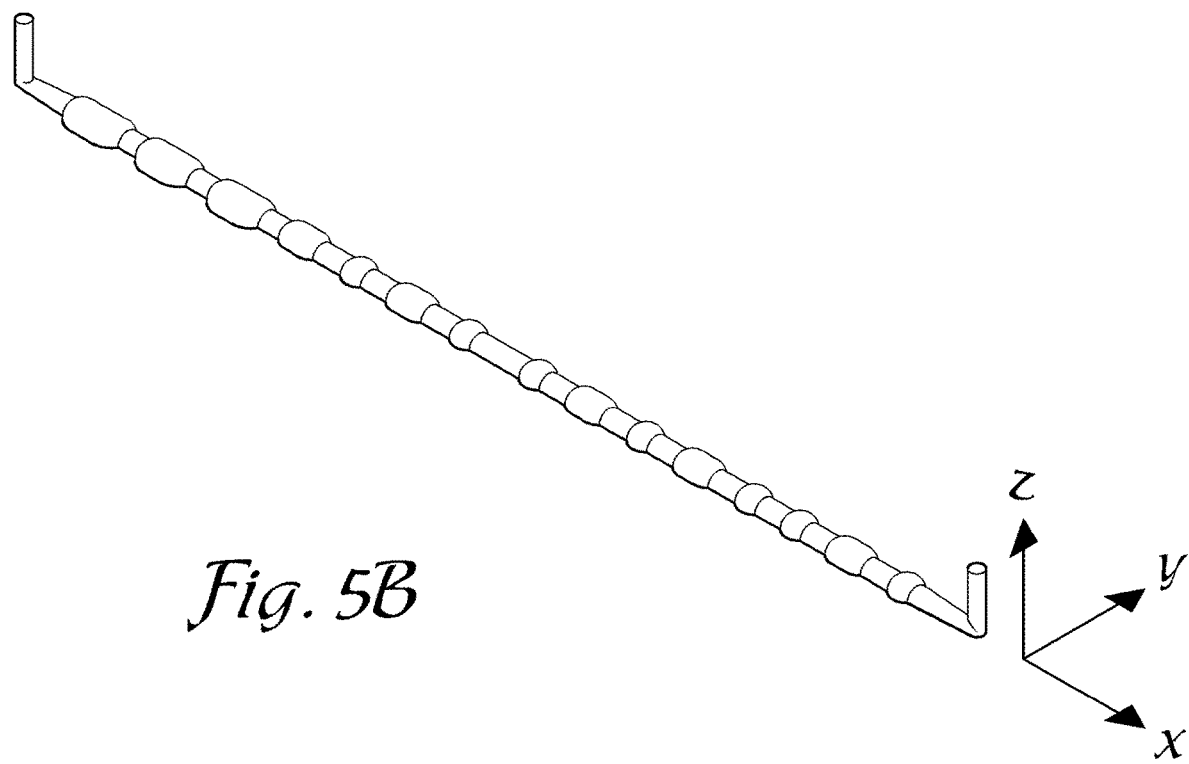
FIG. 5B is an inverted perspective view of FIG. 5A showing the fluid pathway from beneath the pathway.

The above listed parameters are measured by many blood analyzers. FIG. 5A reveals a perspective view of how the fluid would appear as it traverses, in the X direction, through the contoured fluid pathway 48 of the sensor cartridge base 40. As previously discussed, the fluid pathway increases in the Y and Z directions, growing larger in both dimensions, when in proximity to the analyte sensors 20 and lessens, decreasing in dimension in the Y and Z directions, when traversing between the sensors 20 thereby minimizing the sample volume necessary to perform the analysis. FIG. 5B reveals a view from beneath the fluid path providing additional detail on the narrowing and widening profile of the fluid pathway 48. Where there are no sensors in the fluid path, there are no sensor surface area requirements thereby allowing the fluid path to lessen dimensionally as detailed immediately above.

In operation, the fluid, typically blood, is withdrawn from a patient generally via a syringe or other standard blood draw technique. As previously detailed, the blood draw is very minimal in volume, generally no greater than 30 µl. The fluid 50 is then aspirated into the fluid inlet port 42. Upon entering the fluid inlet port 42, the fluid 50 traverses along the contoured fluid pathway 48. This traverse along the fluid pathway 48 places the fluid beneath one, and preferably a multitude of analyte sensors 20, capable of detecting either a change in voltage or amperage.

The diverging and converging of the fluid pathway minimizes the overall volume of fluid required for proper operation of the sensor assembly 10. The change in voltage or amperage at the analyte sensors (ion-selective electrodes) is relayed to the analyte sensor contacts 54 mounted to the sensor panel 14. The change in voltage, or amperage, detected at the analyte sensors 20 is then transmitted from the sensor contacts 54 to the analyzer (not shown). The analyzer, based upon a proprietary algorithm determines the concentrations of the fluid (blood) constituents and other parameters such as blood gases.

Many different arrangements of the various components depicted, as well as components not shown, are possible without departing from the spirit and scope of the disclosed technology. Embodiments of the disclosed technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosed technology.

It will be understood that certain features and sub combinations are of utility and may be employed without reference to other features and sub combinations and are contemplated within the scope of the claims. Not all steps listed in the various figures need be carried out in the specific order described.

I claim:

1. A sensor assembly for analysis of physical parameters and chemical constituents of small volume samples of bodily fluids, the assembly comprising:
    a sensor panel with an upper surface and a lower surface and at least two analyte sensors located on the lower surface, wherein each analyte sensor has a surface area for contacting the bodily fluid for analysis thereof; and
    a sensor cartridge base having an inset bed on which the sensor panel is disposed, the inset bed having a contoured fluid pathway formed therein that extends from a fluid inlet to a fluid outlet, the contoured fluid pathway having a first wall with a first upper edge and a second wall with a second upper edge, wherein the first and second upper edges are in contact with the lower surface of the sensor panel and thereby allow at least a portion of the surface area of each analyte sensor to be brought into contact with fluid when the fluid is traversing along the contoured fluid pathway; and
    wherein the contoured fluid pathway has an analyte sensor area that corresponds to each of the at least two analyte sensors of the sensor panel and at least one transition area that is disposed between two analyte sensor areas, and wherein at least one dimension of each analyte sensor area is greater than a corresponding dimension of at least one transition area; and
    wherein the contoured fluid pathway has a volumetric capacity between the fluid inlet and the fluid outlet in a range of from about 20 µl to about 35 µl.

2. The sensor assembly of claim 1, wherein the sensor panel has at least two analyte sensor contacts per analyte sensor.

3. The sensor assembly of claim 2, wherein the analyte sensor contacts are located on the upper surface of the sensor panel and are laterally and oppositely disposed from one another across the contoured fluid pathway.

4. The sensor assembly of claim 1, wherein the contoured fluid pathway has a first dimension along an X coordinate axis that defines a length of the contoured fluid pathway between the fluid input and the fluid output, a second dimension along a Y coordinate axis that defines a width of the contoured fluid pathway, and a third dimension along a Z coordinate axis that defines a depth of the contoured fluid pathway.

5. The sensor assembly of claim 4, wherein the contoured fluid pathway increases in the Y direction in at least one analyte sensor area.

6. The sensor assembly of claim 4, wherein the contoured fluid pathway increases in the Z direction in at least one analyte sensor area.

7. The sensor assembly of claim 4, wherein the contoured fluid pathway increases in the Y and Z directions in at least one analyte sensor area.

8. The sensor assembly of claim 1, wherein a distance between the first and second upper edges of the contoured fluid pathway in an analyte sensor area is in a range of from about 0.3 mm to about 0.6 mm, and wherein a distance between the first and second upper edges of the contoured fluid pathway in a transition area is in a range of from about 0.1 mm to about 0.25 mm.

9. The sensor assembly of claim 1, wherein each of the at least two analyte sensors is selected from the group consisting of a partial pressure of carbon dioxide ($pCO_2$), a partial pressure of oxygen ($O_2$), blood urea nitrogen (BUN), creatinine (Cre), sodium ($Na^+$), potassium ($K^+$), calcium ($Ca^{2+}$), magnesium ($Mg^{2+}$), lactate (Lac), glucose (Glu), chloride ($Cl^+$), hematocrit, cholesterol, pyruvate, and pH.

10. A sensor assembly for analysis of physical parameters and chemical constituents of small volume samples of bodily fluids, the assembly comprising:
    a sensor panel with an upper surface and a lower surface and at least two analyte sensors located on the lower surface, wherein each analyte sensor has a surface area for contacting the bodily fluid for analysis thereof;
    a sensor cartridge base having an inset bed with a contoured fluid pathway formed therein that extends from a fluid inlet to a fluid outlet, the contoured fluid pathway having a first wall with a first upper edge and a second wall with a second upper edge, wherein the contoured fluid pathway has an analyte sensor area that corresponds to each of the at least two analyte sensors of the sensor panel and at least one transition area that is disposed between two analyte sensor areas, and wherein at least one dimension of each analyte sensor area is greater than a corresponding dimension of at least one transition area;
    an adhesive layer with an upper surface, a lower surface, and a contoured fluid pathway cutout, wherein the upper surface of the adhesive layer is adhesively secured to the lower surface of the sensor panel and the lower surface of the adhesive layer is adhesively secured to the inset bed of the sensor cartridge base, thereby securing the sensor panel to the sensor cartridge base; and
    wherein the contoured fluid pathway cutout of the adhesive layer mirrors a shape and span of the contoured fluid pathway of the sensor cartridge base and thereby allow at least a portion of the surface area of each analyte sensor to be brought into contact with fluid when the fluid is traversing along the contoured fluid pathway; and
    wherein the contoured fluid pathway has a volumetric capacity between the fluid inlet and the fluid outlet in a range of from about 20 µl to about 35 µl.

11. The sensor assembly of claim 10, wherein the sensor panel has at least two analyte sensor contacts per analyte sensor.

12. The sensor assembly of claim 11, wherein the analyte sensor contacts are located on the upper surface of the sensor panel and are laterally and oppositely disposed from one another across the contoured fluid pathway.

13. The sensor assembly of claim 10, wherein the contoured fluid pathway has a first dimension along an X coordinate axis that defines a length of the contoured fluid pathway between the fluid input and the fluid output, a second dimension along a Y coordinate axis that defines a width of the contoured fluid pathway, and a third dimension along a Z coordinate axis that defines a depth of the contoured fluid pathway.

14. The sensor assembly of claim 13, wherein the contoured fluid pathway increases in the Y direction in at least one analyte sensor area.

15. The sensor assembly of claim 13, wherein the contoured fluid pathway increases in the Z direction in at least one analyte sensor area.

16. The sensor assembly of claim 13, wherein the contoured fluid pathway increases in the Y and Z directions in at least one analyte sensor area.

17. The sensor assembly of claim 10, wherein a distance between the first and second upper edges of the contoured fluid pathway in an analyte sensor area is in a range of from about 0.3 mm to about 0.6 mm, and wherein a distance between the first and second upper edges of the contoured fluid pathway in a transition area is in a range of from about 0.1 mm to about 0.25 mm.

18. The sensor assembly of claim 10, wherein each of the at least two analyte sensors is selected from the group consisting of a partial pressure of carbon dioxide ($pCO_2$), a partial pressure of oxygen ($O_2$), blood urea nitrogen (BUN), creatinine (Cre), sodium ($Na^+$), potassium ($K^+$), calcium ($Ca^{2+}$), magnesium ($Mg^{2+}$), lactate (Lac), glucose (Glu), chloride ($Cl^+$), hematocrit, cholesterol, pyruvate, and pH.

* * * * *